United States Patent
Sun

(10) Patent No.: US 10,555,681 B2
(45) Date of Patent: Feb. 11, 2020

(54) MUSCLE MASSAGING DEVICE AND OPERATING METHOD THEREOF

(71) Applicant: BOE TECHNOLOGY GROUP CO., LTD., Beijing (CN)

(72) Inventor: Mengmeng Sun, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 975 days.

(21) Appl. No.: 15/096,607

(22) Filed: Apr. 12, 2016

(65) Prior Publication Data
US 2017/0007487 A1    Jan. 12, 2017

(30) Foreign Application Priority Data

Jul. 10, 2015  (CN) .......................... 2015 1 0405596

(51) Int. Cl.
*A61H 15/02* (2006.01)
*A61B 5/04* (2006.01)
(Continued)

(52) U.S. Cl.
CPC ........ *A61B 5/04012* (2013.01); *A61B 5/0488* (2013.01); *A61B 5/1107* (2013.01); *A61B 5/224* (2013.01); *A61F 7/02* (2013.01); *A61H 15/02* (2013.01); *A61H 23/02* (2013.01); *A61H 39/04* (2013.01); *A61F 2007/0039* (2013.01); *A61F 2007/0088* (2013.01); *A61H 15/0078* (2013.01); *A61H 2015/0042* (2013.01); *A61H 2201/0207* (2013.01); *A61H 2201/164* (2013.01); *A61H 2201/165* (2013.01);
(Continued)

(58) Field of Classification Search
CPC ... A61B 5/04012; A61B 5/1107; A61H 23/02; A61H 2205/102; A61H 2201/5097; A61H 2201/5007; A61H 2201/1654; A61H 2201/165; A61H 2201/164; A61F 7/02
See application file for complete search history.

(56) References Cited

U.S. PATENT DOCUMENTS

2005/0159690 A1   7/2005  Barak
2007/0088235 A1*  4/2007  Tseng .................. A61H 9/0078
                                                        601/151
(Continued)

FOREIGN PATENT DOCUMENTS

CN       101039641 A      9/2007
CN       102247277 A     11/2011
(Continued)

OTHER PUBLICATIONS

Chinese Office Action dated Sep. 26, 2016.

*Primary Examiner* — Tu A Vo
(74) *Attorney, Agent, or Firm* — Dilworth & Barrese, LLP.; Michael J. Musella, Esq.

(57) ABSTRACT

A muscle massaging device and an operating method thereof are provided. The muscle massaging device, comprising includes: a detector, configured to detect a real-time myoelectric value and a real-time muscle tension value of a target muscle; a comparator, configured to compare the real-time myoelectric value and a prestored myoelectric value, and compare the real-time muscle tension value and a prestored muscle tension value; and a massager, configured to massage a first region corresponding to the target muscle.

14 Claims, 5 Drawing Sheets

(51) Int. Cl.
*A61B 5/11* (2006.01)
*A61F 7/02* (2006.01)
*A61H 23/02* (2006.01)
*A61B 5/0488* (2006.01)
*A61B 5/22* (2006.01)
*A61H 39/04* (2006.01)
*A61F 7/00* (2006.01)
*A61H 15/00* (2006.01)

(52) U.S. Cl.
CPC ............... *A61H 2201/1654* (2013.01); *A61H 2201/5007* (2013.01); *A61H 2205/102* (2013.01); *A61H 2230/085* (2013.01); *A61H 2230/605* (2013.01)

(56) References Cited

U.S. PATENT DOCUMENTS

| | | | | |
|---|---|---|---|---|
| 2009/0221943 | A1* | 9/2009 | Burbank | A61H 1/008 601/46 |
| 2010/0249637 | A1* | 9/2010 | Walter | A61H 23/02 600/544 |
| 2012/0022415 | A1* | 1/2012 | Mullen | A61H 9/0078 601/150 |
| 2012/0265107 | A1* | 10/2012 | Smith | A61H 7/001 601/15 |
| 2012/0304216 | A1* | 11/2012 | Strong | H04N 21/440281 725/25 |
| 2013/0041296 | A1* | 2/2013 | Tass | A61H 7/001 601/15 |
| 2013/0085426 | A1* | 4/2013 | Brodsky | A61H 15/00 601/128 |
| 2013/0090519 | A1* | 4/2013 | Tass | A61H 23/00 600/28 |
| 2013/0218058 | A1* | 8/2013 | Ceoldo | A61H 7/001 601/46 |
| 2014/0330186 | A1* | 11/2014 | Hyde | A61F 5/02 602/19 |
| 2016/0008206 | A1* | 1/2016 | Devanaboyina | A47C 9/002 601/136 |
| 2016/0220808 | A1* | 8/2016 | Hyde | A61N 1/0452 |

FOREIGN PATENT DOCUMENTS

| | | |
|---|---|---|
| CN | 102467228 A | 5/2012 |
| CN | 202314233 U | 7/2012 |
| CN | 202637718 U | 1/2013 |
| CN | 103239350 A | 8/2013 |
| CN | 204744934 U | 11/2015 |

* cited by examiner

MUSCLE MASSAGING DEVICE AND OPERATING METHOD THEREOF

TECHNICAL FIELD

Embodiments of the present disclosure relate to a muscle massaging device and an operating method thereof.

BACKGROUND

A muscle spasm is a phenomenon of a sudden and involuntary tetanus contraction of muscle. For example, in a case of exposure to cold or fatigue (it is prone to the old-aged women), a gastrocnemius muscle of a leg may have the muscle spasm, which causes unbearable pain, and may occur at night sometimes, affecting quality of sleep. Because the spasm is usually a sudden symptom, which is hard to prevent and treat in advance.

An existing muscle spasm therapeutic device used in a hospital, however, often employs a manner of electric shock, which is complicated to operate, difficult to carry, and not applicable to wearing and using at home. In a massage of traditional Chinese medicine, only one acupoint may be massaged every time; even if some massaging devices for relieving the spasm can massage a plurality of acupoints simultaneously, which operates in a manual mode, has a low degree of automation, and is difficult to timely treat the sudden spasm symptom of a patient.

SUMMARY

Embodiments of the present disclosure provide a muscle massaging device and an operating method thereof, which can realize automatic detection of the muscle spasm and automatic massage for relieving the spasm.

In one aspect, an embodiment of the present disclosure provides a muscle massaging device, comprising: a detecting module, configured to detect a real-time myoelectric value and a real-time muscle tension value of a target muscle; a comparing module, configured to compare the real-time myoelectric value and a prestored myoelectric value, and compare the real-time muscle tension value and a prestored muscle tension value; and a massaging module, configured to massage a first region corresponding to the target muscle.

In another aspect, an embodiment of the present disclosure provides an operating method of the muscle massaging device as mentioned above, comprising: S1: detecting a real-time myoelectric value and a real-time muscle tension value of a target muscle; S2: comparing the real-time myoelectric value and a prestored myoelectric value, and comparing the real-time muscle tension value and a prestored muscle tension value; S3: starting the massaging module to massage when a condition that the real-time myoelectric value is greater than or equal to the prestored myoelectric value and/or the real-time muscle tension value is greater than or equal to the prestored muscle tension value is met; and when the condition is not met, returning to step S1.

In another aspect, an embodiment of the present disclosure provides an operating method of the muscle massaging device as mentioned above, comprising: S1: detecting a real-time myoelectric value and a real-time muscle tension value of a target muscle; S2: comparing the real-time myoelectric value and a prestored myoelectric value, and comparing the real-time muscle tension value and a prestored muscle tension value; S3: starting the massaging module to massage when a condition that the real-time myoelectric value is greater than or equal to the prestored myoelectric value and/or the real-time muscle tension value is greater than or equal to the prestored muscle tension value is met, and a first duration of the real-time myoelectric value greater than or equal to the prestored myoelectric value and/or a second duration of the real-time muscle tension value greater than or equal to the prestored muscle tension value are/is greater than a second predetermined time; and returning to step S1 when the condition is not met and the first duration and the second duration are less than the second predetermined time.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Figure 1:
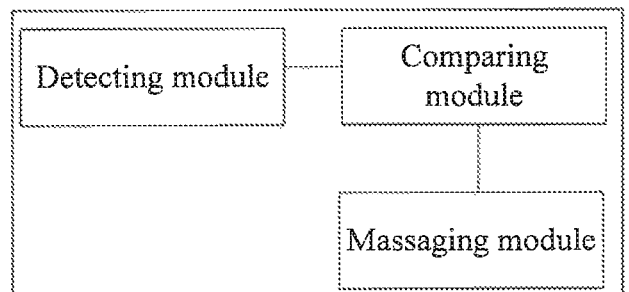
FIG. 1 shows a schematic block diagram of a muscle massaging device according to an embodiment of the present disclosure.

As shown in FIG. 1, a muscle massaging device 100 according to an embodiment of the present disclosure comprises:

A detecting module 11, configured to detect a real-time myoelectric value and a real-time muscle tension value of a target muscle;

A comparing module 12, configured to compare the real-time myoelectric value and a prestored myoelectric value, and compare the real-time muscle tension value and a prestored muscle tension value;

A massaging module 13, configured to massage a first region corresponding to the target muscle, according to a comparison result of the comparing module 12, under a condition that the real-time myoelectric value is greater than or equal to the prestored myoelectric value and/or the real-time muscle tension value is greater than or equal to the prestored muscle tension value.

By comparing the real-time myoelectric value and the prestored myoelectric value, and/or comparing the real-time muscle tension value and the prestored muscle tension value, in accordance with the two muscle parameters, it may be accurately determined whether the target muscle has a spasm, and then a first region (e.g., an acupoint corresponding to the target muscle) is massaged timely, so that automatic detection of muscle spasm is realized, and automatic massage for relieving the spasm is realized, which is especially applicable to providing convenient and intelligent massage service for a person with reduced mobility (e.g., the elders, the pregnant women, etc.).

It should be noted that, here the first region corresponding to the target muscle may include at least one sub region, for example, for a gastrocnemius muscle, the first region includes sub regions corresponding to a Yanglingquan acupoint, a Tiaokou acupoint, a Weizhong acupoint, a Chengj in acupoint and/or a Chengshan acupoint.

In the embodiment of the present disclosure, at least one sub region, for example, two or more sub-regions may be automatically massaged at the same time, thereby realizing automatic muscle massage.

Figure 3:
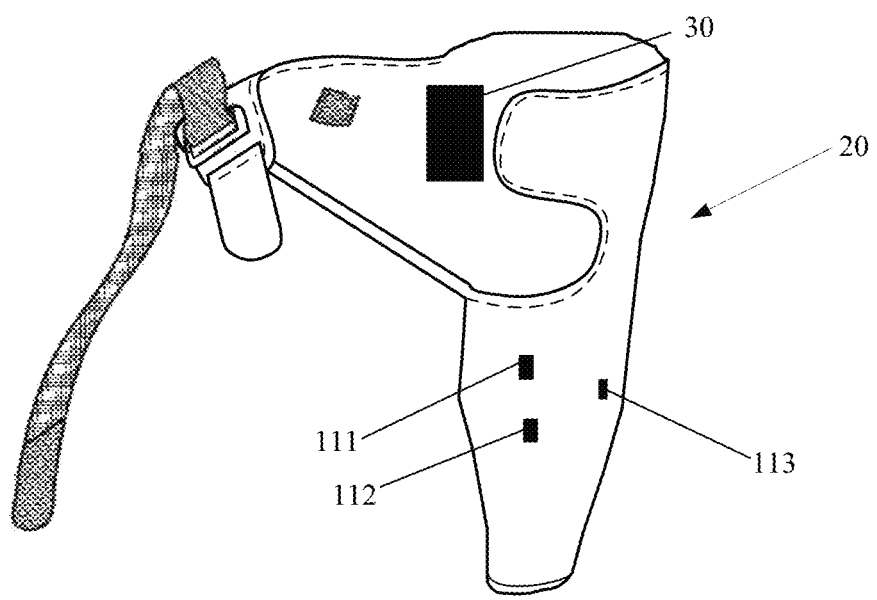
FIG. 3 shows a structural schematic diagram of a sleeving piece according to an embodiment of the present disclosure.

Exemplarily, as shown in FIG. 3, the muscle massaging device 100 may further comprises:

A sleeving piece 20 corresponding to a limb where the target muscle is located, is used for sleeving the limb, so as to improve portability and enhance operability.

Wherein, the detecting module 11, the comparing module 12 and the massaging module 13 may be arranged on the sleeving piece 20, for example, may be integrated into an integrated circuit 30, and the integrated circuit 30 may be sandwiched in the sleeving piece 20, to prevent limbs from damage by friction.

The muscle massaging device may be sleeved with the limb through the sleeving piece 20, so as to facilitate a user wearing. FIG. 3 only shows one shape of the sleeving piece 20, and the sleeving piece 20 may be set according to an actual sleeving position, for example, it may be set in an arm-like shape, or a waist-like shape. The sleeving piece 20 may be of a closed ring, and the sleeving piece 20 is worn by putting the limb into the sleeving piece 20; and the sleeving piece 20 may further be of a planar shape, it is sleeved with the limb by bending to fit the limb and buckling a connecting part.

Exemplarily, the massaging module 13 may include:

At least one massaging ball 131 made of an elastic material, arranged on an inner wall of the sleeving piece 20, and protruding towards an inner side of the sleeving piece 20 when the real-time myoelectric value is greater than or equal to the prestored myoelectric value, and/or the real-time muscle tension value is greater than or equal to the prestored muscle tension value, so as to massage the first region.

In one aspect, the massaging ball 131 protrudes towards the inner side of the sleeving piece 20 only when performing massage, and in a non-working state it may keep alignment with the inner wall of the sleeving piece 20, which may not affect normal movement of a user.

In another aspect, acupoints may be better massaged in a massaging manner of protruding, and thus a spasm symptom of the target muscle may be rapidly relieved; and a radius of the massaging ball may be set to 0.5 cm, wherein an electro-motor is built-in for driving the massaging ball 131 to massage.

The massaging ball 131 is made of an elastic material, so the target muscle may not be damaged when protruding towards an inner side of the sleeving piece.

Exemplarily, the massaging module 13 may further include:

a heating unit 132, releasing heat to the target muscle when the real-time myoelectric value is greater than or equal to the prestored myoelectric value, and/or the real-time muscle tension value is greater than or equal to the prestored muscle tension value.

The heating unit 132 may be arranged independently, or may be arranged inside the massaging ball 131; for example, a heating unit 132 is arranged inside each massaging ball 131, and through the heating unit 132, the first region may conduct heat therapy when the massaging ball massages the first region, to accelerate relieving the spasm symptom. The heating unit 132 may be an infrared neon light.

Exemplarily, for different target muscle, the first region to be massaged, that is, corresponding acupoint is different, so setting position of the massaging ball 131 is different, and at this time, the massaging ball 131 may be designed to be connected to the muscle massaging device 100 by a connecting line, and the muscle massaging device 100 may be positioned at the corresponding first region and then is fixed for massaging.

Exemplarily, each massaging ball 131 may be correspondingly provided with one heating unit, and a number of the heating units may be one or more, and may be greater or less than the number of the massaging balls, which is not limited by the embodiment of the present disclosure.

Figure 2:
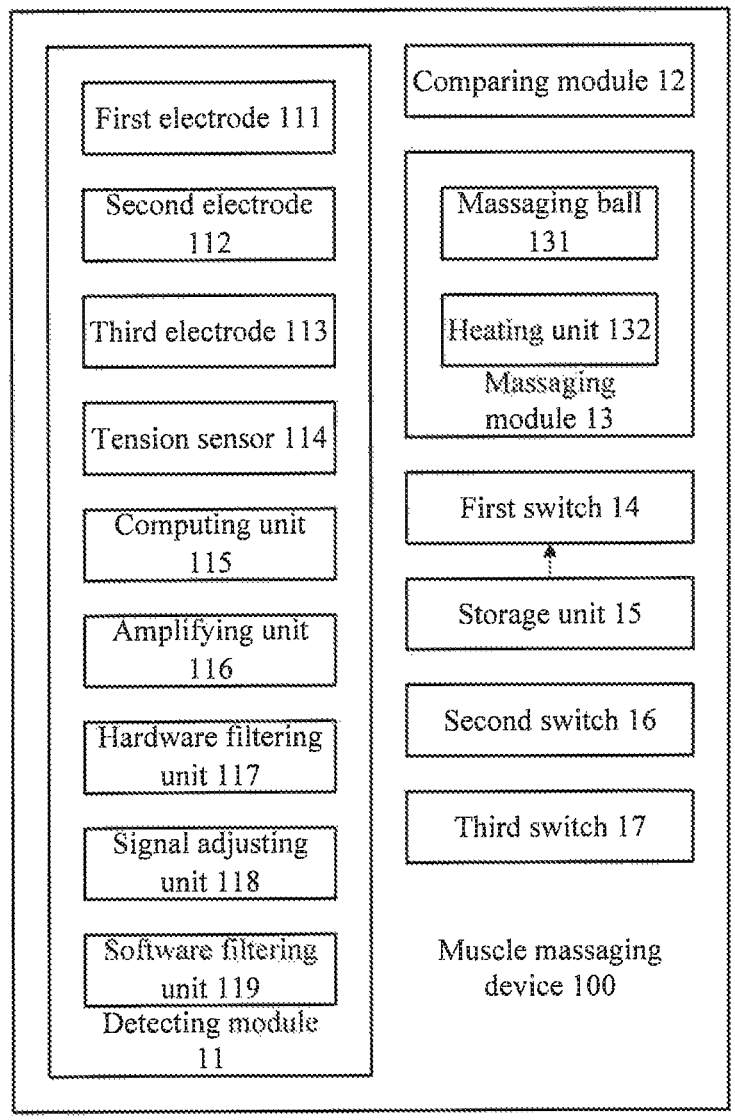
FIG. 2 shows a schematic block diagram of a muscle massaging device according to an embodiment of the present disclosure.

Exemplarily, as shown in FIG. 2, the detecting module 11 may include a first electrode 111, a second electrode 112, a third electrode 113, a tension sensor 114 and a computing unit 115, wherein, the first electrode 111 and the second electrode 112 are arranged on both sides of a preset point on an inner wall of the sleeving piece 20, the preset point corresponding to a central point of the target muscle, and are used for detecting a first muscle electric signal and a second muscle electric signal, respectively.

The third electrode 113 is arranged on a side of the inner wall of the sleeving piece 20 away from the preset point, and is used for detecting a third muscle electric signal.

For example, the target muscle is a gastrocnemius muscle, and then the preset point corresponds to a central point of the gastrocnemius muscle, the first electrode 111 and the second electrode 112 may be arranged at, for example, 1 cm from the preset point above/below, respectively, which may be attached to a muscle belly of the gastrocnemius muscle in parallel when detecting the muscle electric signal.

The computing unit 115 is used for calculating the real-time myoelectric value according to the first muscle electric signal, the second muscle electric signal and the third muscle electric signal, for example, it may be calculated by a formula of:

$$\text{Mean square root RMS} = \sqrt{\frac{\sum_{n=1}^{N} x_i^2}{N}}$$

Where, $x_i$ is a myoelectric value calculated according to the first muscle electric signal, the second muscle electric signal and the third muscle electric signal every time, N is a number of detecting (e.g., 5 times) in a short period (e.g., 2 s); a mean square root of the myoelectric values detected serves as a real-time myoelectric value, which may avoid misoperation caused by change of instantaneous myoelectric value of the muscle due to unexpected cases, thereby making a massaging response accurately.

The tension sensor 114 is used for detecting the real-time muscle tension value of the target muscle.

The muscle electric signal may be accurately detected by arranging the electrodes in the above manner. In FIG. 3, for convenience of illustration, the first electrode 111, the second electrode 112 and the third electrode 113 are marked on an outer side of the sleeving piece 20, and in fact, the first electrode 111, the second electrode 112 and the third electrode 113 are located on an inner side of the sleeving piece 20.

Exemplarily, the detecting module 11 may further include:

an amplifying unit 116, for amplifying the first muscle electric signal, the second muscle electric signal and the third muscle electric signal;

a hardware filtering unit 117, for performing hardware filtering on the amplified first muscle electric signal, the second muscle electric signal and the third muscle electric signal;

a signal adjusting unit 118, for adjusting the first muscle electric signal, the second muscle electric signal and the third muscle electric signal after the hardware filtering;

a software filtering unit 119, for performing software filtering on the adjusted first muscle electric signal, the second muscle electric signal and the third muscle electric signal, wherein, the computing unit 115 is used for calculating a real-time myoelectric value according to the first muscle electric signal, the second muscle electric signal and the third muscle electric signal after the software filtering.

A disturbing signal may be filtered and removed from the first muscle electric signal, the second muscle electric signal and the third muscle electric signal through pre-amplifying, hardware filtering, adjusting and software filtering, so that signals input into the computing unit 115 are more regular, facilitating the accurating calculation of the computing unit 115.

Exemplarily, the muscle massaging device according to an embodiment of the present disclosure further comprises: a first switch 14 and a storage unit 15, Wherein, when the first switch 14 is closed, a prestored myoelectric value is acquired, the storage unit 15 is controlled to acquire a plurality of myoelectric values calculated by the computing unit 115 when a user is in different postures and acquire a plurality of muscle tension values calculated by the tension sensor 114 when the user is in different postures, and a maximum value in the plurality of myoelectric values is used as the prestored myoelectric value, a maximum value in the plurality of muscle tension values is used as the prestored muscle tension value.

Different postures of a user may include a state that the target muscle is relaxing, a state that the target muscle is tensioning and a state that the target muscle is half tensioning; more comprehensive data related to the target muscle of the user may be obtained by obtaining the myoelectric values and the muscle tension values under a condition of the target muscle is in different states, and thus more accurate response may be made.

In a general muscle spasm, a myoelectric value is greater than or equal to that in the tensioning state, and a muscle tension value is greater than or equal to that in the tensioning state, and therefore, a maximum myoelectric value in the plurality of myoelectric values is used as the prestored myoelectric value, and a maximum muscle tension value in the plurality of muscle tension values is used as the prestored muscle tension value, which ensures that a massage operation is performed only when the target muscle spasm occurs, so as to avoid misoperation.

Exemplarily, the user may set the prestored myoelectric value and the prestored muscle tension value according to the following steps:

At first, the first switch 14 is closed, and then a myoelectric value and a muscle tension value in a lying down state (i.e., a relaxing state) are acquired, and finally a myoelectric value and a muscle tension value are acquired in a tensioning state, for example, a squatting state; every acquisition may last 10 s, a prompt sound or a prompt light may be sent after the acquisition is finished, and finally, the prestored myoelectric value which is a maximum myoelectric value in the plurality of myoelectric values and the prestored muscle tension value which is a maximum muscle tension value in the plurality of muscle tension values are stored.

Figure 4:
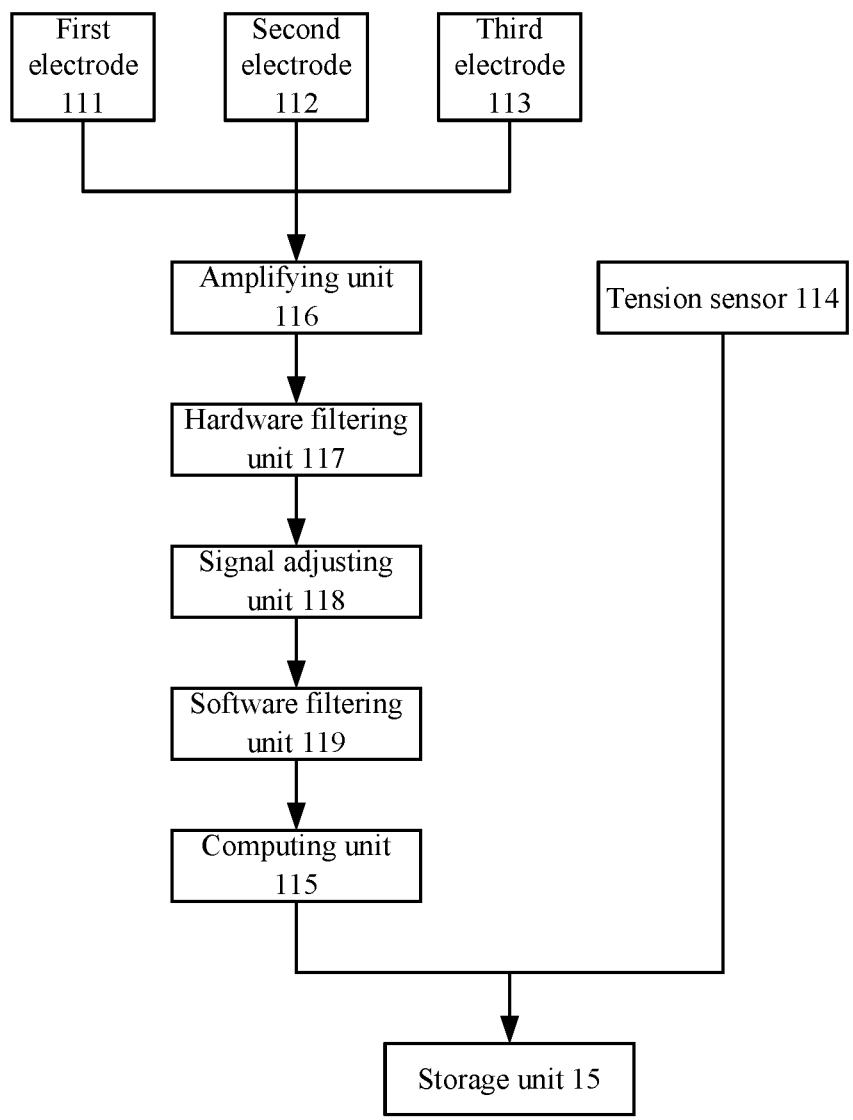
FIG. 4 shows a schematic diagram of a signal flow direction according to an embodiment of the present disclosure.

A signal flow direction of the prestored myoelectric value and the prestored muscle tension value which are stored in the storage unit 15 is shown in FIG. 4, wherein the acquired myoelectric value and muscle tension value should be subjected to an analog-to-digital conversion, which will not be repeated here.

Exemplarily, the muscle massaging device according to the embodiment of the present disclosure may further comprise:

a second switch 16, when closed, the detecting module is controlled to detect a real-time myoelectric value and a real-time muscle tension value of a target muscle and the storage unit 15 is controlled to stop acquiring data from the computing unit.

When the detecting module 11 is detecting, the device 10 is in a normal operating state, the storage unit 15 may be controlled to stop setting the prestored myoelectric value and the prestored muscle tension value, which avoids data of the detecting operation and the setting operation being mixed.

Figure 5:
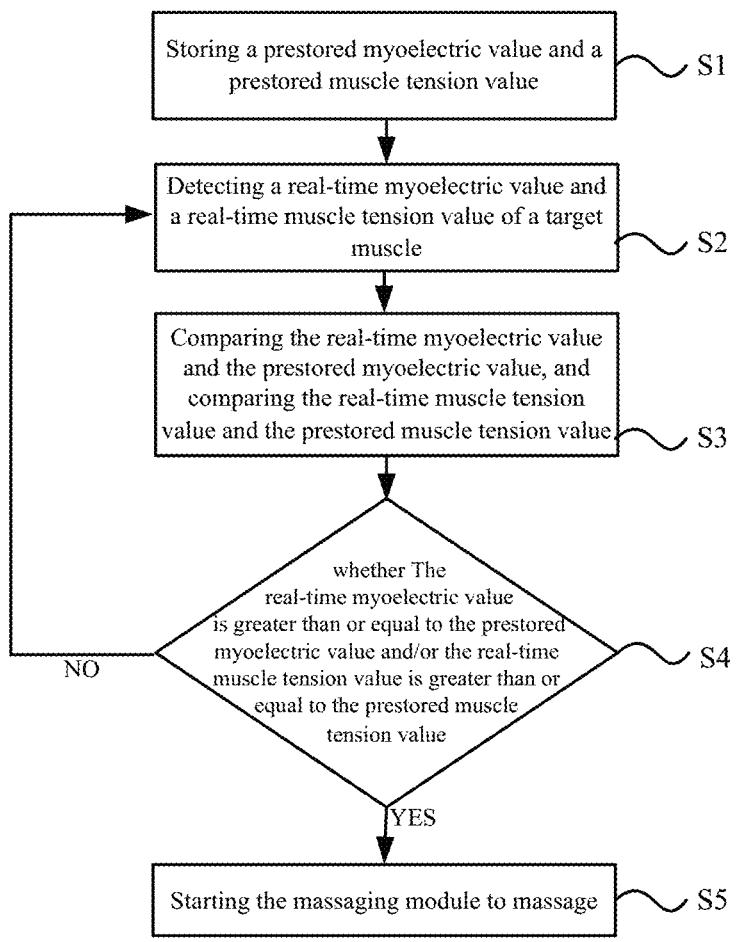
FIG. 5 shows a flow chart of detecting spasm and massaging operation according to an embodiment of the present disclosure.

The detecting process may be as shown in FIG. 5:

S1: storing a prestored myoelectric value and a prestored muscle tension value;

S2: detecting a real-time myoelectric value and a real-time muscle tension value of a target muscle;

S3: comparing the real-time myoelectric value and the prestored myoelectric value, and comparing the real-time muscle tension value and the prestored muscle tension value;

S4: determining whether the real-time myoelectric value is greater than or equal to the prestored myoelectric value and/or the real-time muscle tension value is greater than or equal to the prestored muscle tension value, and proceeding to S5 under a condition that the real-time myoelectric value is greater than or equal to the prestored myoelectric value and/or the real-time muscle tension value is greater than or equal to the prestored muscle tension value, or returning to S2;

S5: starting the massaging module to massage.

Exemplarily, the muscle massaging device may further comprises:

a third switch 17, when closed, the storage unit 15 is controlled to reset the prestored myoelectric value and the prestored muscle tension value.

Since there are differences between the myoelectric values and the muscle tension values of different users, when the device 10 is applied to different users, the storage unit 15 may be controlled by the third switch 17 to reset the prestored myoelectric value and the prestored muscle tension value therein, so as to re-acquire data and set the prestored myoelectric value and the prestored muscle tension value, further realizing an accurate and timely detection and response.

Exemplarily, the massaging module 13 massages the first region for a first predetermined time, when the real-time myoelectric value is greater than or equal to the prestored myoelectric value, and/or the real-time muscle tension value is greater than or equal to the prestored muscle tension value.

When the real-time myoelectric value detected by the detecting module 11 after the first predetermined time is less than the prestored myoelectric value, and the detected real-time muscle tension value is less than the prestored muscle tension value, it indicates that the spasm symptom has been relieved, and the massaging module 13 stops massaging the first region.

When the real-time myoelectric value detected by the detecting module 11 after the first predetermined time is greater than or equal to the prestored myoelectric value, and/or the detected real-time muscle tension value is greater than or equal to the prestored muscle tension value, it indicates that the spasm symptom has not been relieved, and the massaging module 13 continues massaging the first region.

When the real-time myoelectric value detected by the detecting module after the first predetermined time is less than the prestored myoelectric value, and the detected real-time muscle tension value is less than the prestored muscle tension value, it indicates that the spasm symptom has been relieved, and thus the massaging operation of the massaging module may be automatically stopped, so as to save electrical energy. When the real-time myoelectric value detected by the detecting module after the first predetermined time is greater than or equal to the prestored myoelectric value, and/or the detected real-time muscle tension value is greater than or equal to the prestored muscle tension value, it indicates that the target muscle is in a spasm state, so that the massaging module may continue massaging, to fully relieve the spasm of the target muscle. Wherein, the first predetermined time, for example, may be 3 min, and of course, may be specifically determined according to actual needs.

Exemplarily, when the real-time myoelectric value is greater than or equal to the prestored myoelectric value, and/or the real-time muscle tension value is greater than or equal to the prestored muscle tension value, the massaging module 13 is further configured to determine whether durations of the real-time myoelectric value and/or the real-time muscle tension value are greater than or equal to a second predetermined time, and if yes, massage the first region.

There may be a situation that the real-time myoelectric value of the target muscle is greater than or equal to the prestored myoelectric value, and/or the real-time muscle tension value is greater than or equal to the pre-stored muscle tension value due to an external stimulation, however, such situation is not a case where the target muscle has a spasm, and such situation often lasts for a short time period. By determining whether durations of the real-time myoelectric value and/or the real-time muscle tension value are greater than or equal to a second predetermined time, the massaging operation may be only performed when the target muscle has a spasm, which improves responsive accuracy of the massaging operation.

Figure 6:
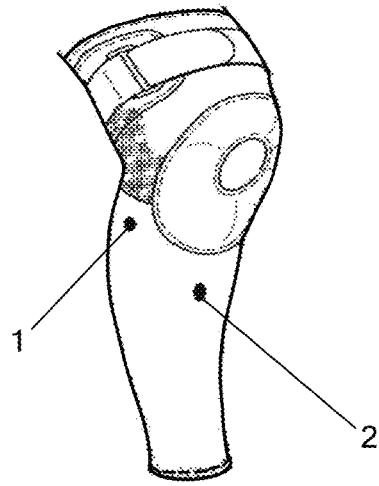
FIG. 6 and FIG. 7 show schematic diagrams of acupoints according to an embodiment of the present disclosure.
Figure 7:
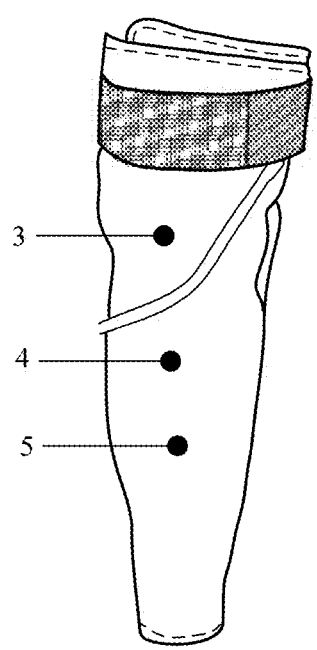

Exemplarily, the target muscle may be a gastrocnemius muscle, as shown in FIG. 6 and FIG. 7, the first region may include a Yanglingquan acupoint 1, a Tiaokou acupoint 2, a Weizhong acupoint 3, a Chengjin acupoint 4 and/or a Chengshan acupoint 5.

When the gastrocnemius muscle has a spasm, the spasm symptom of the gastrocnemius muscle may be rapidly relieved by massaging the Yanglingquan acupoint 1, the Tiaokou acupoint 2, the Weizhong acupoint 3, the Chengjin acupoint 4 and/or the Chengshan acupoint 5.

Hereinabove, technical solutions of the embodiments of the present disclosure are described in detail in conjunction with the accompanying drawings, considering that in the prior art, it is hard to effectively and timely treat the spasm symptom of a patient. Through the technical solution of the present disclosure, the real-time myoelectric value and a pre-stored myoelectric value may be compared, and the real-time muscle tension value and a pre-stored muscle tension value may be compared, and in accordance with the two muscle parameters, it may be accurately determined whether the target muscle has a spasm, and thus a first region is massaged timely, so that automatic detection of the muscle spasm is realized, and automatic massage for relieving the spasm is realized, which is especially applicable to providing convenient and intelligent massage service for a person with reduced mobility.

In the embodiments of the present disclosure, terms "first", "second", and "third" are used only for the purpose of description, but cannot be understood as indicating or implying relative importance. The term "a plurality of" refers to two or more, unless otherwise defined expressly.

The invention claimed is:

1. A muscle massaging device, comprising:
   a detector, configured to detect a real-time myoelectric value and a real-time muscle tension value of a target muscle;
   a comparator, configured to compare the real-time myoelectric value and a prestored myoelectric value, and compare the real-time muscle tension value and a prestored muscle tension value;
   a massager, configured to massage a first region corresponding to the target muscle,
   wherein the muscle massaging device further comprises:
   a sleeving piece corresponding to a limb where the target muscle is located, which is used for sleeving the limb,
   the detector is arranged on the sleeving piece,
   wherein the detector comprises: a first electrode, second electrode, a third electrode, a tension sensor and a computer,
   wherein, the first electrode and the second electrode are arranged on opposite sides of a preset point on an inner wall of the sleeving piece, the preset point corresponding to a central point of the target muscle, and the first electrode and the second electrode are used for detecting a first muscle electric signal and a second muscle electric signal, respectively;
   the third electrode is arranged on a side of the inner wall of the sleeving piece away from the preset point, and is used for detecting a third muscle electric signal;
   the computer is used for calculating the real-time myoelectric value according to the first muscle electric signal, the second muscle electric signal and the third muscle electric signal;
   the tension sensor is used for detecting the real-time muscle tension value of the target muscle, wherein the muscle massaging device further comprising: a first switch and a storage unit, wherein, when the first switch is closed, the storage unit is controlled to acquire a plurality of myoelectric values calculated by the computer when a user is in different postures and acquire a plurality of muscle tension values detected by the tension sensor when the user is in different postures, and the computer is configured to select a maximum value in the plurality of myoelectric values to use as the prestored myoelectric value, and select a maximum value in the plurality of muscle tension values to use as the prestored muscle tension value, and wherein the massager is configured to massage the first region based on the real-time myoelectric value and the real-time muscle tension value.

2. The muscle massaging device according to claim 1, wherein the comparator and the massager are arranged on the sleeving piece.

3. The muscle massaging device according to claim 2, wherein the massager comprises:
at least one massaging ball, made of an elastic material, arranged on an inner wall of the sleeving piece, and protruding towards an inner side of the sleeving piece under a condition that the real-time myoelectric value is greater than or equal to the prestored myoelectric value, and/or the real-time muscle tension value is greater than or equal to the prestored muscle tension value, so as to massage the first region.

4. The muscle massaging device according to claim 3, wherein the massager further comprises:
a heater, releasing heat to the target muscle under a condition that the real-time myoelectric value is greater than or equal to the prestored myoelectric value, and/or the real-time muscle tension value is greater than or equal to the prestored muscle tension value.

5. The muscle massaging device according to claim 1, wherein the detector further comprises:
an amplifier, for amplifying the first muscle electric signal, the second muscle electric signal and the third muscle electric signal;
a hardware filter, for performing hardware filtering on the amplified first muscle electric signal, the amplified second muscle electric signal and the amplified third muscle electric signal;
a signal adjuster, for adjusting the first muscle electric signal, the second muscle electric signal and the third muscle electric signal after the hardware filtering;
a software filter, for performing software filtering on an adjusted first muscle electric signal, an adjusted second muscle electric signal and an adjusted third muscle electric signal.

6. The muscle massaging device according to claim 1, further comprising:
a second switch, wherein when the second switch is closed, the detector is controlled to detect the real-time myoelectric value and the real-time muscle tension value of the target muscle and the storage unit is controlled to stop acquiring data from the computer.

7. The muscle massaging device according to claim 6, further comprising:
a third switch, wherein when the third switch is closed, the storage unit is controlled to reset the prestored myoelectric value and the prestored muscle tension value.

8. The muscle massaging device according to claim 1, wherein the massager massages the first region for a first predetermined time, under a condition that the real-time myoelectric value is greater than or equal to the prestored myoelectric value, and/or the real-time muscle tension value is greater than or equal to the prestored muscle tension value,
the massager stops massaging the first region, under a condition that the real-time myoelectric value detected by the detector after the first predetermined time is less than the prestored myoelectric value, and the detected real-time muscle tension value is less than the prestored muscle tension value,
the massager continues massaging the first region, under a condition that the real-time myoelectric value detected by the detector after the first predetermined time is greater than or equal to the prestored myoelectric value, and/or the detected real-time muscle tension value is greater than or equal to the prestored muscle tension value.

9. The muscle massaging device according to claim 1, wherein, under a condition that the real-time myoelectric value is greater than or equal to the prestored myoelectric value, and/or the real-time muscle tension value is greater than or equal to the prestored muscle tension value, the massager is further configured to determine whether duration of the real-time myoelectric value is greater than or equal to a predetermined time and/or duration of the real-time muscle tension value is greater than or equal to the predetermined time, and under a condition that the duration of the real-time myoelectric value is greater than or equal to the predetermined time and/or the duration of the real-time muscle tension value is greater than or equal to the predetermined time, the first region is massaged.

10. The muscle massaging device according to claim 1, wherein the target muscle is gastrocnemius muscle, the first region including a Yanglingquan acupoint, a Tiaokou acupoint, a Weizhong acupoint, a Chengjin acupoint and/or a Chengshan acupoint.

11. An operating method of the muscle massaging device according to claim 1, comprising the steps of:
S1: detecting the real-time myoelectric value and the real-time muscle tension value of the target muscle;
S2: comparing the real-time myoelectric value and the prestored myoelectric value, and comparing the real-time muscle tension value and the prestored muscle tension value;
S3: starting the massager to massage when a condition that the real-time myoelectric value is greater than or equal to the prestored myoelectric value and/or the real-time muscle tension value is greater than or equal to the prestored muscle tension value is met; and when the condition is not met, returning to step S1.

12. The operating method according to claim 11, before step S1, further comprising:
storing the prestored myoelectric value and the prestored muscle tension value.

13. An operating method of the muscle massaging device according to claim 1, comprising the steps of:
S1: detecting the real-time myoelectric value and the real-time tension value of a target muscle;
S2: comparing the real-time myoelectric value and the prestored myoelectric value, and comparing the real-time muscle tension value and the prestored muscle tension value;
S3: starting the massager to massage when a condition that the real-time myoelectric value is greater than or equal to the prestored myoelectric value and/or the real-time muscle tension value is greater than or equal to the prestored muscle tension value is met, and a first duration of the real-time myoelectric value greater than or equal to the prestored myoelectric value and/or a second duration of the real-time muscle tension value greater than or equal to the prestored muscle tension value are/is greater than a predetermined time; and returning to step S1 when the condition is not met and the first duration and the second duration the predetermined are less than the predetermined time.

14. The operating method according to claim 13, before step S1, further comprising:

storing the prestored myoelectric value and the prestored muscle tension value.

\* \* \* \* \*